(12) United States Patent
Agui et al.

(10) Patent No.: US 9,121,792 B1
(45) Date of Patent: Sep. 1, 2015

(54) SYSTEM AND APPARATUS FOR FILTERING PARTICLES

(75) Inventors: Juan H Agui, Strongsville, OH (US); Rajagopal Vijayakumar, Liverpool, NY (US)

(73) Assignee: The United States of America as Represented by the Administrator of National Aeronautics and Space Administration, Washington, DC (US)

(*) Notice: Subject to any disclaimer, the term of this patent is extended or adjusted under 35 U.S.C. 154(b) by 215 days.

(21) Appl. No.: 13/527,181

(22) Filed: Jun. 19, 2012

(51) Int. Cl.
*G01N 1/22* (2006.01)
*G01N 15/02* (2006.01)

(52) U.S. Cl.
CPC ...... *G01N 1/2208* (2013.01); *G01N 2001/2223* (2013.01); *G01N 2015/0261* (2013.01)

(58) Field of Classification Search
CPC .............. G01N 1/2208; G01N 1/2223; G01N 2015/0261

USPC .................... 73/863.22, 28.05, 28.06, 863.21
See application file for complete search history.

(56) References Cited

U.S. PATENT DOCUMENTS

| | | | | |
|---|---|---|---|---|
| 4,321,822 A | * | 3/1982 | Marple et al. ................. | 73/28.06 |
| 5,906,752 A | * | 5/1999 | Williams ....................... | 210/783 |
| 5,932,795 A | * | 8/1999 | Koutrakis et al. ............ | 73/28.01 |
| 6,431,014 B1 | * | 8/2002 | Liu et al. ...................... | 73/863.22 |
| 6,938,777 B2 | * | 9/2005 | Call et al. ...................... | 209/143 |
| 8,689,648 B1 | * | 4/2014 | Heff ............................ | 73/863.22 |
| 2010/0242632 A1 | * | 9/2010 | Call ............................ | 73/863.22 |

* cited by examiner

*Primary Examiner* — Hezron E Williams
*Assistant Examiner* — David Z Huang
(74) *Attorney, Agent, or Firm* — Robert H. Earp, III (57) ABSTRACT

A modular pre-filtration apparatus may be beneficial to extend the life of a filter. The apparatus may include an impactor that can collect a first set of particles in the air, and a scroll filter that can collect a second set of particles in the air. A filter may follow the pre-filtration apparatus, thus causing the life of the filter to be increased.

9 Claims, 11 Drawing Sheets

SYSTEM AND APPARATUS FOR FILTERING PARTICLES

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

FIELD

The present invention relates to a filtration device, and more particularly, to an impactor and filter system configured to capture a plurality of particles.

BACKGROUND

During long duration human space flights in space crafts, human habitation in extraterrestrial habitats, such as the International Space Station, and in terrestrial applications such as commercial aircrafts, remote instrument enclosures, or a submarine, clean air is required for occupants such as astronauts, equipment, passengers or submarine crew. Maintaining cleanliness of the air requires filtration systems that have a long working life and are designed to filter several decades of different particle sizes. When a large dust load and a wide range of particle sizes are to be removed, it is a common commercial practice to use a multi-stage filtration system with a first stage that removes the largest particles. Since the largest fraction of dust in the air stream reduces the life of a filter, a pre-filter for large particles may be beneficial to protect the more expensive or critical filters designed for higher efficiencies and smaller particles.

However, the biggest challenge for long duration deployment is the difficulty of maintenance during service. For example, maintaining of the filter may be limited based on limited availability of the crew, crew time, and/or resources. Another challenge is to limit the footprint and payload while still providing the flexibility needed for the system to be tailored to the filtration needs of any mission or commercial application. Current space or commercial filtration devices do not provide a multi-year life or a small payload required for space.

SUMMARY

Certain embodiments of the present invention may provide solutions to the problems and needs in the art that have not yet been fully identified, appreciated, or solved by current filtration devices. For example, certain embodiments of the present invention are directed to a filter system that includes a pre-filter stage to protect the more expensive or critical and higher efficiency stages of the filter system. The pre-filter stage increases the life of the filter system.

In one embodiment, an apparatus includes an impactor plate and a plurality of bands. The impactor plate includes a plurality of orifices that allow air to traverse through the plurality of orifices. Each band is located near the impactor plate, and is configured to collect particles in the air.

In another embodiment, an apparatus includes a supply spool and a receiving spool. The supply spool is configured to unwind material over a plurality of rollers and the receiving spool can wind the material. The material is configured to collect particles, as air traverses through the apparatus.

In yet another embodiment, an apparatus includes an impactor and a scroll filter. The impactor is configured to collect a first set of particles in the air, and the scroll filter is configured to collect a second set of particles in the air.

BRIEF DESCRIPTION OF THE DRAWINGS

For a proper understanding of the invention, reference should be made to the accompanying figures. These figures depict only some embodiments of the invention and are not limiting of the scope of the invention. Regarding the figures.

DETAILED DESCRIPTION OF THE EMBODIMENTS

Figure 1A:
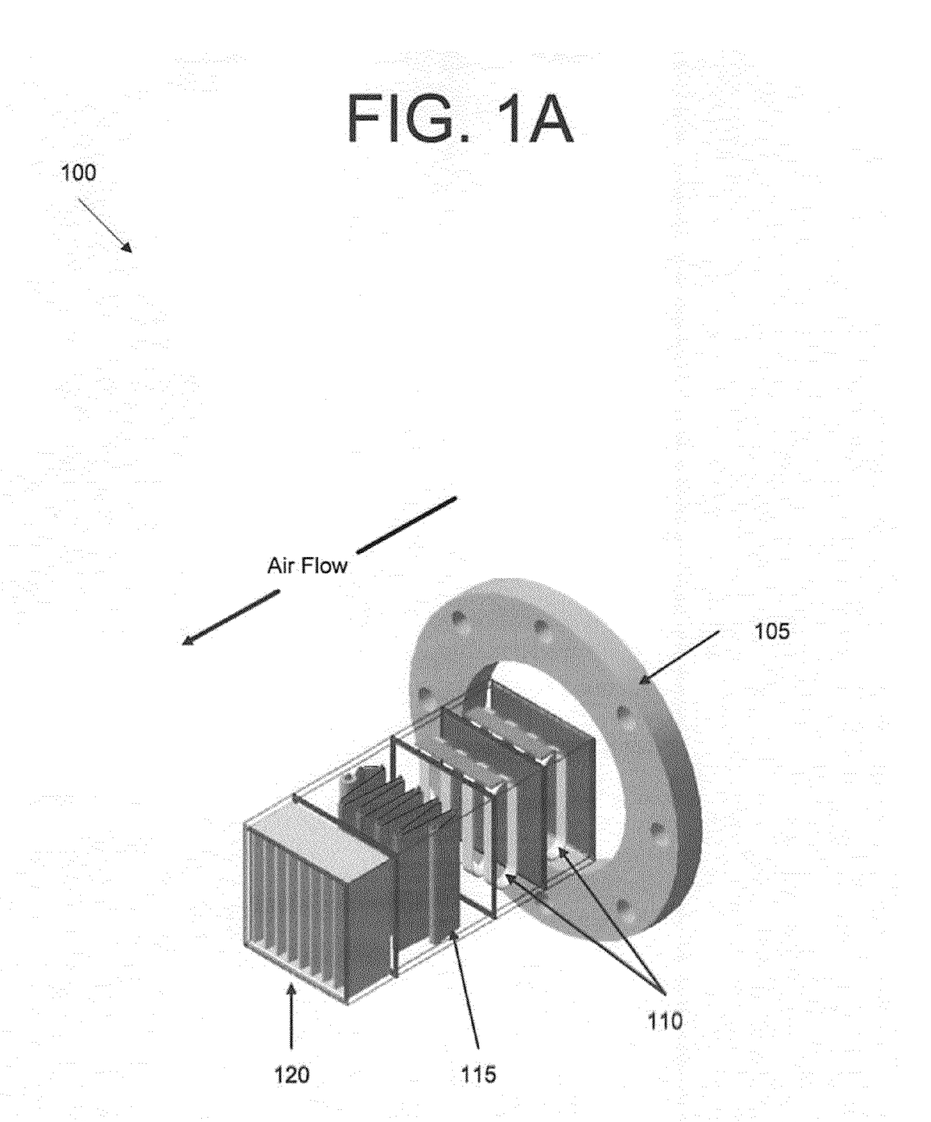
FIGS. 1A and 1B illustrate a first view and a second view of a multi-stage filter, according to an embodiment of the present invention.
Figure 1B:
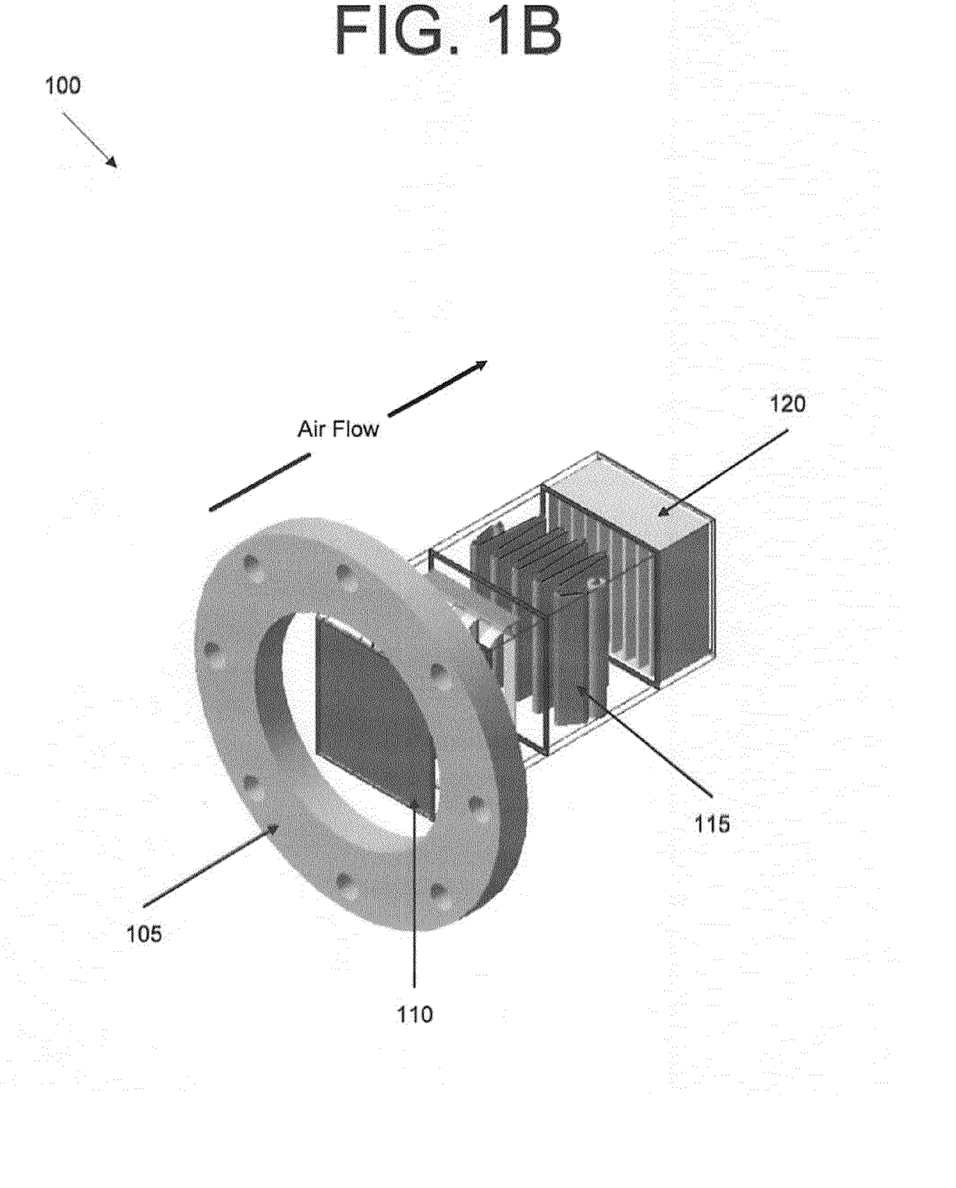

Embodiments of the present invention provide an apparatus configured to capture particles of different sizes utilizing one or more impactors and/or scroll filters. FIGS. 1A and 1B illustrate a first view and a second view of a multi-stage filter 100, according to an embodiment of the present invention. In this embodiment, multi-stage filter 100 is shown for open flow purposes without an inlet and outlet manifold, and may be used to efficiently filter both larger and smaller particles, thus increasing the life of, for example, a high-efficiency particulate arresting (HEPA) filter 120. Multi-stage filter 100 in this embodiment includes, for example, a mounting flange 105, two impactors 110, a scroll filter 115, and HEPA filter 120. It should be appreciated that certain embodiments may include one or more impactor stages 110 and/or one or more scroll filters 115 as pre-filtration devices. Impactors 110 and scroll filter 115 may act as a pre-filtration device prior to air flowing into, for example, HEPA filter 120. Furthermore, the size of impactors 110 and scroll filter 115 may be scalable to any size, or the material may be changed in scroll filter 115, as would be appreciated by a person of ordinary skill in the art. For example, the size of impactors 110 and scroll filter 115 may be scaled for residential, commercial, or industrial purposes, as well as spaceflight purposes, and as such, all embodiments are not limited to use in space. In another example, the quality of the material in scroll filter 115 may be changed depending on the efficiency desired in multi-stage filter 100.

Figure 2:
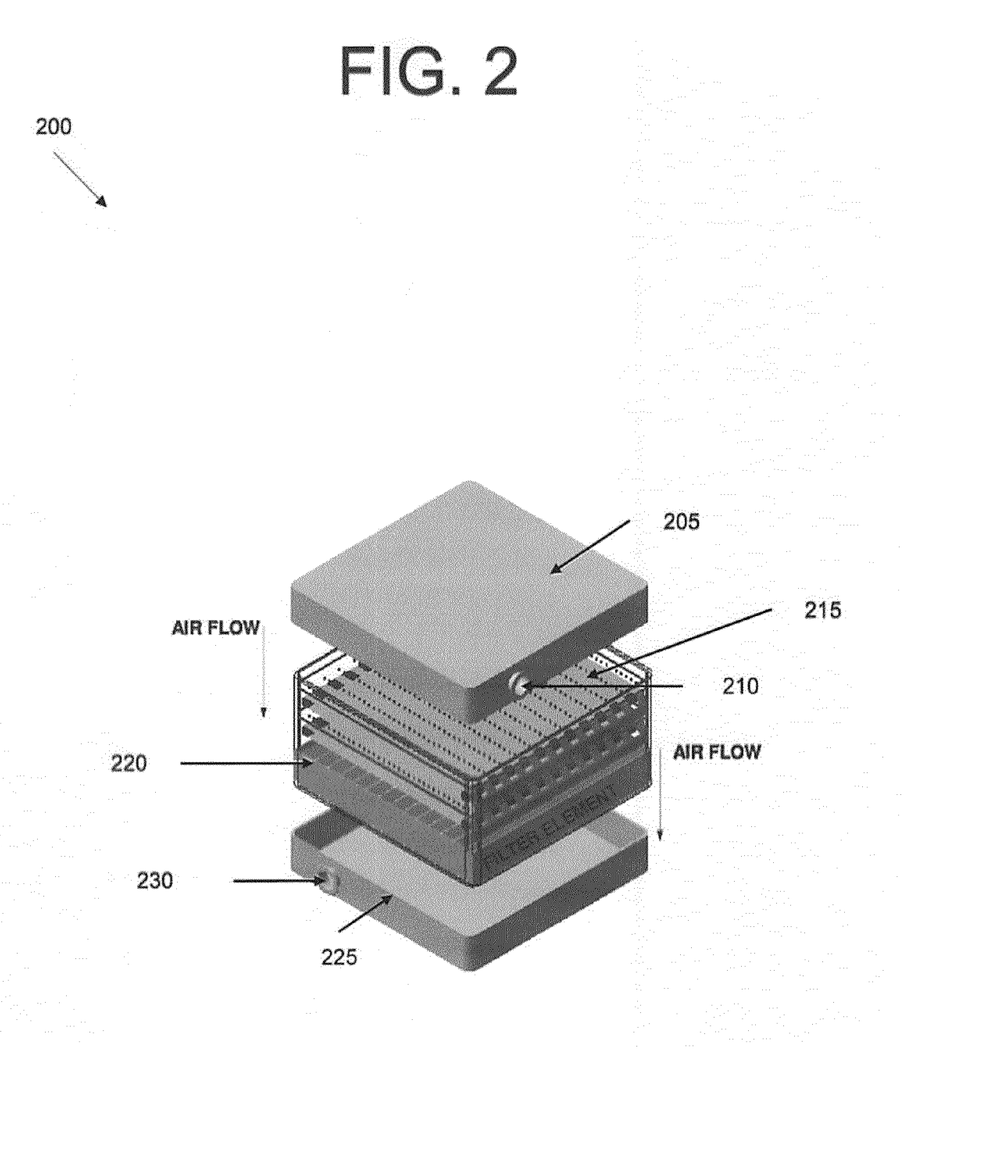
FIG. 2 illustrates a multi-stage filter, according to an embodiment of the present invention.

FIG. 2 illustrates a multi-stage filter 200, according to an embodiment of the present invention. Multi-stage filter 200 may be used as a pre-filtration device. For example, air may flow through inlet 210 of a first cover plate (or manifold) 205, and may flow through two stages of impactors 215, as well as a scroll filter 220. As will be discussed in greater detail below, impactors 215 and scroll filter 220 may be configured to capture or collect different sizes of particles as air traverses through multi-stage filter 200. For example, impactors 215 may capture larger particles, and scroll filter 220 may capture smaller or nano particles. As impactors 215 and scroll filter 220 capture particles, the air may exit through outlet 230 of a second cover plate 225 and then flow to a filtering device, such as a HEPA filter or any other filtration device. Such a multi-stage pre-filtration device may improve the longevity of, for example, the HEPA filter.

Figure 3:
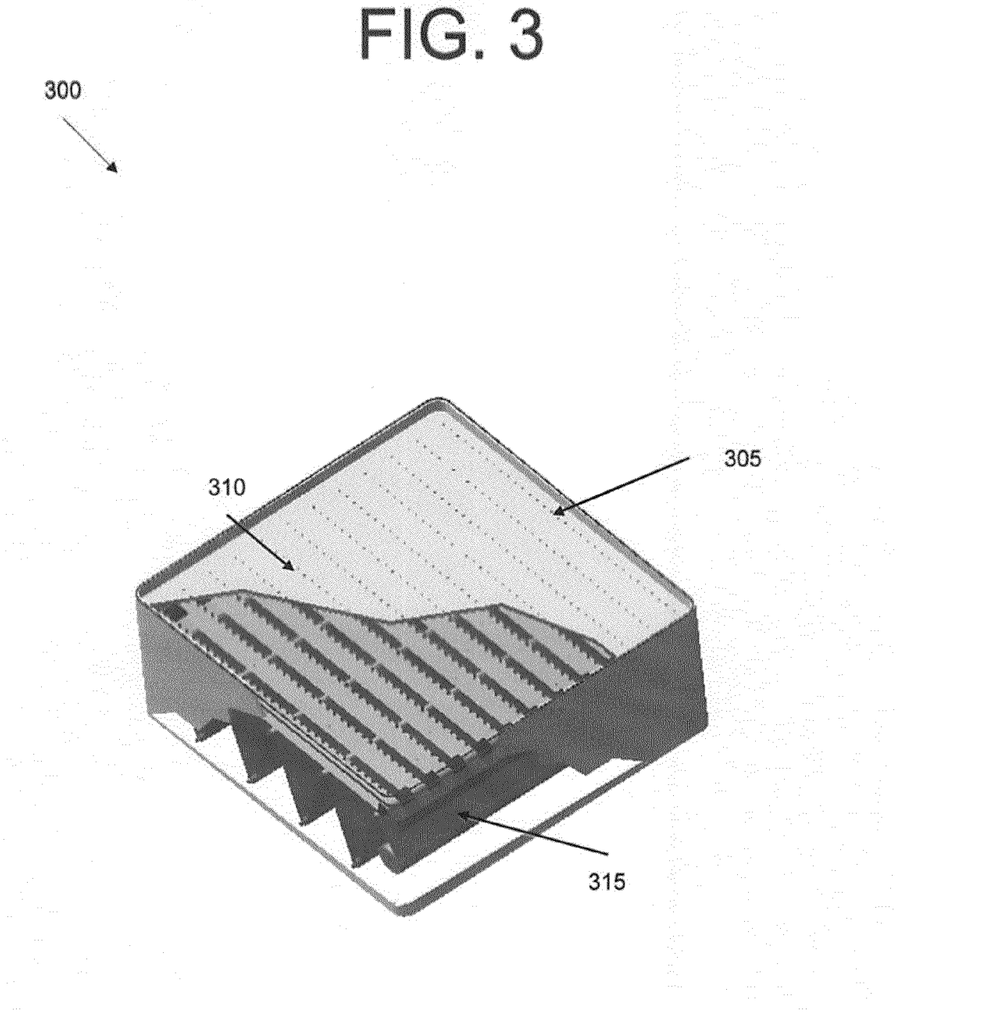
FIG. 3 illustrates a top-view of the multi-stage filter shown in FIG. 2, according to an embodiment of the present invention.

FIG. 3 illustrates a top-view 300 of multi-stage filter 200 shown in FIG. 2, according to an embodiment of the present invention. Top-view 300 shows an impactor 305 containing a plurality of orifices 310, such as holes or slits, to capture larger particles. While this embodiment depicts a plurality of holes 310, impactor 305 may contain rectangular slits instead. It should be appreciated that the shape and size of the orifices or slits is a matter of design choice. Top-view 300 also shows a scroll filter 315 configured to capture smaller sized particles. It should be appreciated that the arrangement of the impactors and scroll filters shown in FIGS. 1-3 may be implementation-specific, or configured in any arrangement that would be appreciated by a person of ordinary skill in the art.

Figure 4:
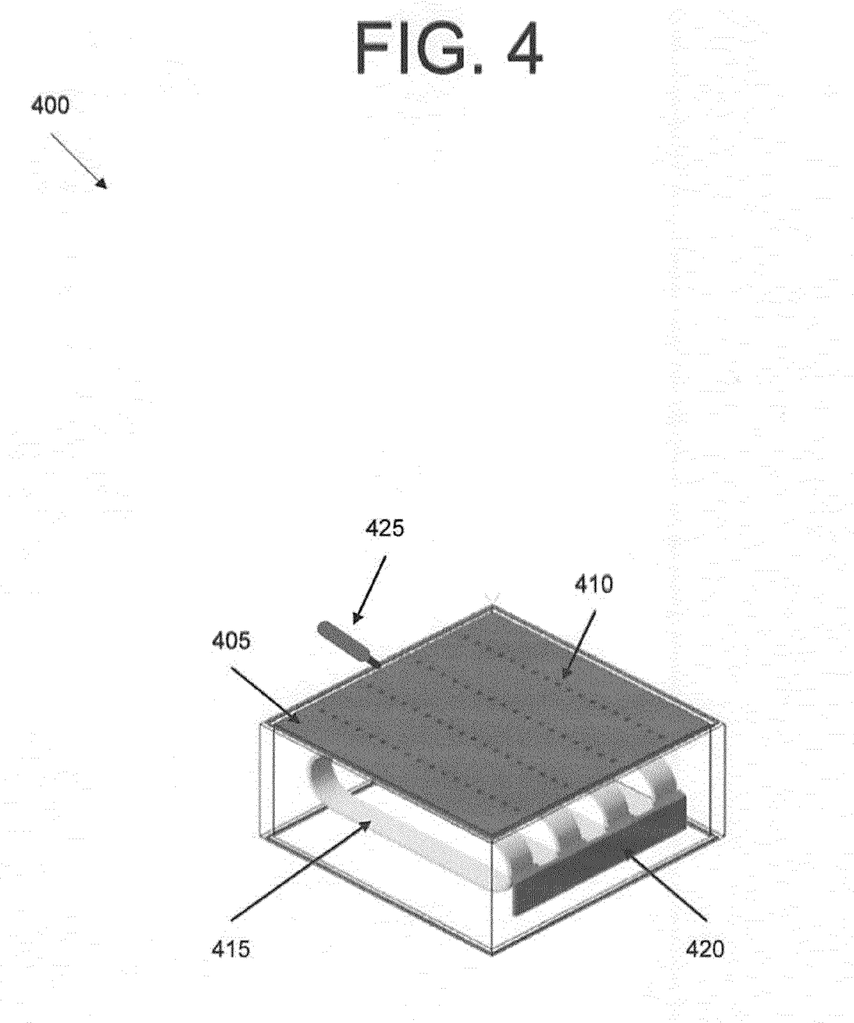
FIG. 4 illustrates an impactor, according to an embodiment of the present invention.

FIG. 4 illustrates an impactor 400, according to an embodiment of the present invention. Impactor 400 includes an impactor plate 405 containing a plurality of orifices 410. Depending on the size and shape of the particles that are to be removed, the size of orifices 410 may be increased or decreased in situ. In some embodiment, impactor plate 405 may include an adjusting unit 425. Adjusting unit 425 may be configured to adjust the size and shape of plurality of orifice 410 in situ for performance changes in impactor 400. For example, adjusting unit 425 may change the size or shape of the holes, slits, or any opening on impactor plate 405 at any time during operation of impactor 400. While impactor plate 405 includes a plurality of holes in this embodiment, impactor plate 405 may include rectangular slits, triangular slits, or any opening as would be appreciated by a person of ordinary skill in the art to capture larger and/or smaller sized particles.

A gap (not shown) exists between impactor plate 405 and a plurality of collector belts 415. The gap, as more clearly shown in FIG. 5, allows air to traverse through orifices 410 while larger sized particles are captured on each collector belt 415. Collector belts 415 may be located beneath orifices 410 to allow maximum collection of particles. Depending on the size of the gap and/or orifices, different sizes of particles can be captured by collector belts 415. While FIG. 4 shows four collector belts, other embodiments may include more or less than four collector belts.

Each collector belt 415 may be a rolling band of material, otherwise called an endless collector belt. To increase the life of each collector belt 415 and to minimize particles that are bound to each collector belt 415, the material of each collector belt 415 may be made of porous material, or any material, to collect particles in the depth of collector belt 415 rather than the surface, thereby eliminating the need for tackifiers. Each collector belt 415 may be driven by a servo (not shown) that moves each collector belt 415 in either a left or right direction when particle buildup is detected.

Figure 7:
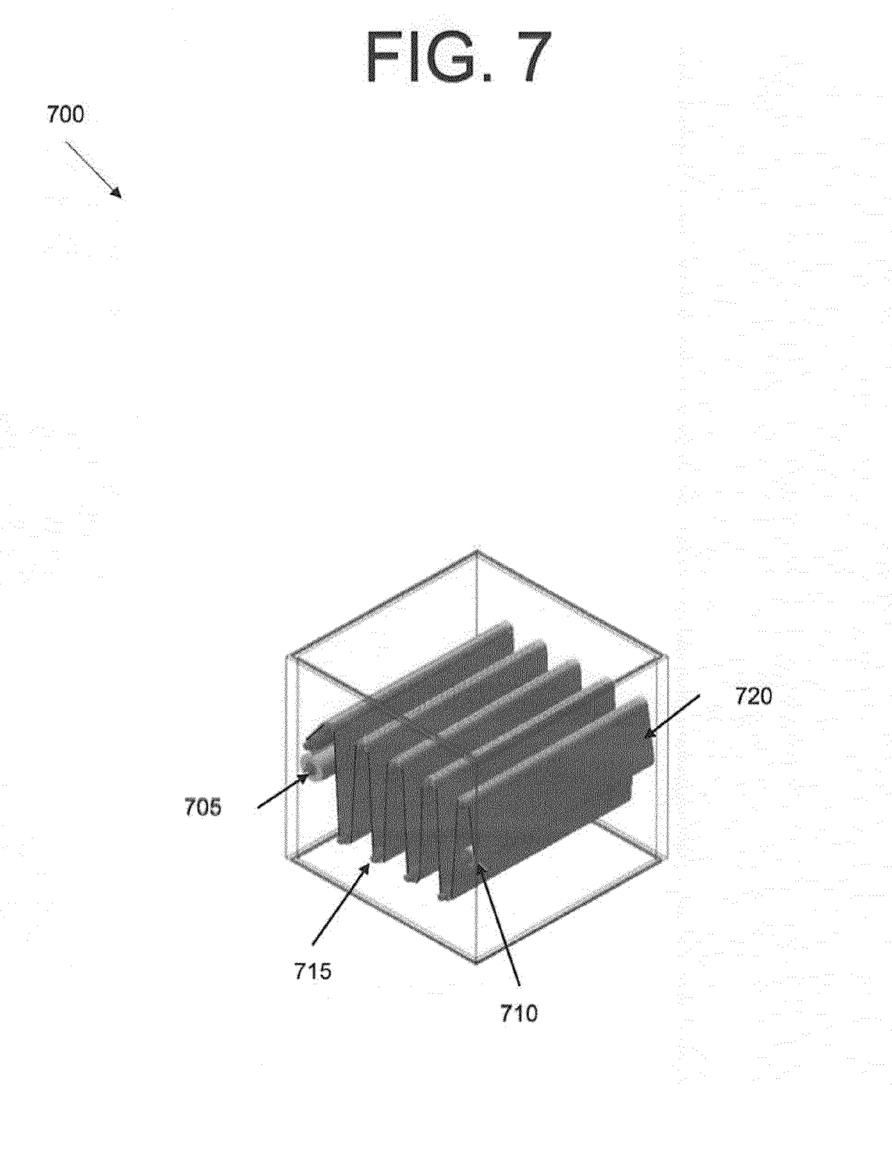
FIG. 7 illustrates a scroll filter, according to an embodiment of the present invention.

Collector belt 415 may include individual and endless bands of material in one embodiment, and in another embodiment, may include individual bands that may be wound and unwound utilizing a plurality of rollers similar to the embodiment shown in FIG. 7. In certain embodiments, however, collector belt 415 may include bands that are connected together in a sheet of material, i.e., a sheet with alternate bands of solid material to collect particles and open mesh material for air to pass through similar to a patterned lace. In yet another embodiment, collector belt 415 may include a sheet that may be endless or wound and unwound. A person of ordinary skill in the art will readily appreciate that collector belt 415 may include different embodiments or combination of embodiments as discussed herein.

In conventional systems, each time a collector plate is filled up with particles, the collector plate is replaced or the entire system is replaced. This not only increases cost of maintaining the system, but also produces an inefficient operation of the system and reduces effective duty life between clean up. In this embodiment, rather than replacing each collector belt 415 when particle buildup occurs, each collector belt 415 may be indexed and dust scraper 420 may scrape particles from each collector belt 415 in order to allow each collector belt 415 to be used again. In certain embodiments, collector belts 415 with particle buildup may be indexed, while other collector belts 415 without particle buildup may remain unindexed. The scraped particles can then be taken to a lab, for example, for analysis purposes. The possibility of removing the collected particles for analysis purposes may offer the potential for investigating the history of the particles collected, and as a result, may be used to refine the design of filtration systems in space habitats, space crafts or commercial applications.

It should be appreciated that impactor 400 may also include a sensor (not shown) to detect when particle buildup occurs on collector belt 415 and, when such buildup occurs, the sensor may transmit a signal to a servo to rotate each collector belt 415 to allow scraper 420 to remove the particle buildup from each collector belt 415. In certain embodiments, the sensor may detect that particle buildup has occurred based on the weight mass, inertia, or other means exerted by the particles on collector belts 415, or based on detection method that would be appreciated by a person of ordinary skill in the art. Such a configuration reduces the cost of replacing impactor 400 each time particle buildup occurs, as well as improves the longevity and efficiency of impactor 400. This configuration may also prevent particle rebounding from occurring, since collector belts 415 are cleaned after a particle buildup occurs and/or after a predetermined period of time.

In addition to virtually permanent filtration, impactor 400 can be tailored to meet any pre-filtration requirement. For example, it should be appreciated that impactor 400 may be stackable, as depicted in FIG. 1. By stacking a plurality of impactors 400 in series, particles of different sizes may be removed more efficiently. In certain embodiments, impactor plate 405 having a plurality of orifices 410 may be interchanged or swapped with another impactor plate having larger or smaller sized orifices, depending on the size of the particle that is targeted. The size and/or material of collector belts 415 may also change accordingly.

Figure 5:
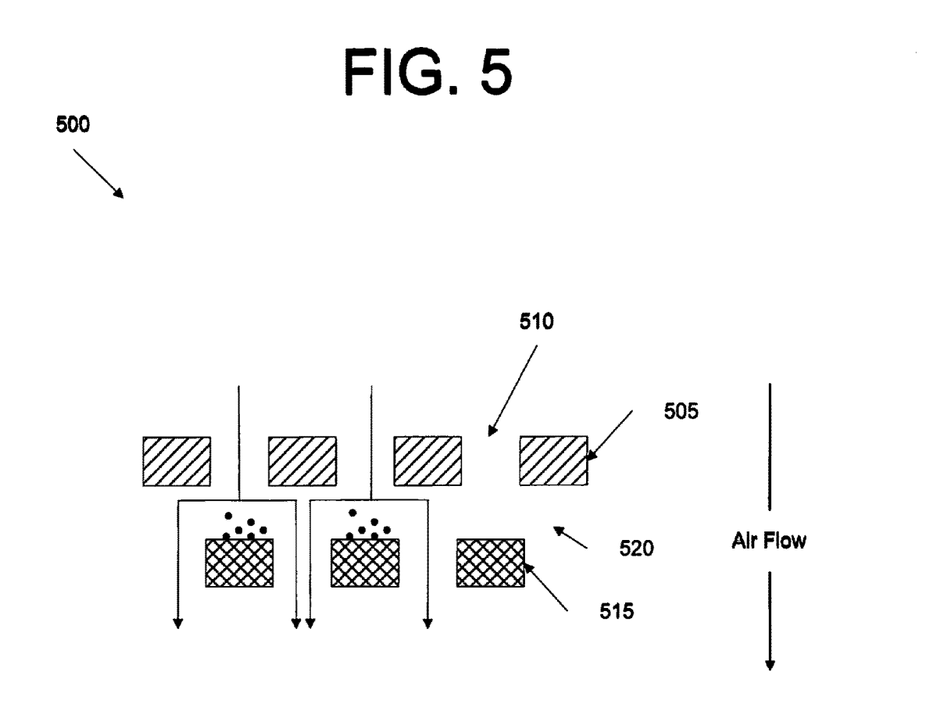
FIG. 5 illustrates a front view of a cross-section of the impactor shown in FIG. 4, according to an embodiment of the present invention.

FIG. 5 illustrates a front view of a cross-section 500 of impactor 400 shown in FIG. 4, according to an embodiment of the present invention. Cross-section 500 shows particles in the air traversing through a plurality of orifices 510 of an impactor plate 505. Gap 520 between impactor plate 505 and collector belts 515 allows the air to flow through impactor 500, while each collector belt 515 captures particles. By placing each collector belt 515 just beneath orifices 510 of impactor plate 505, air is forced to bend around each collector belt 515 and exit to the next filter, while each collector belt 515 captures particles of different sizes.

Figure 6:
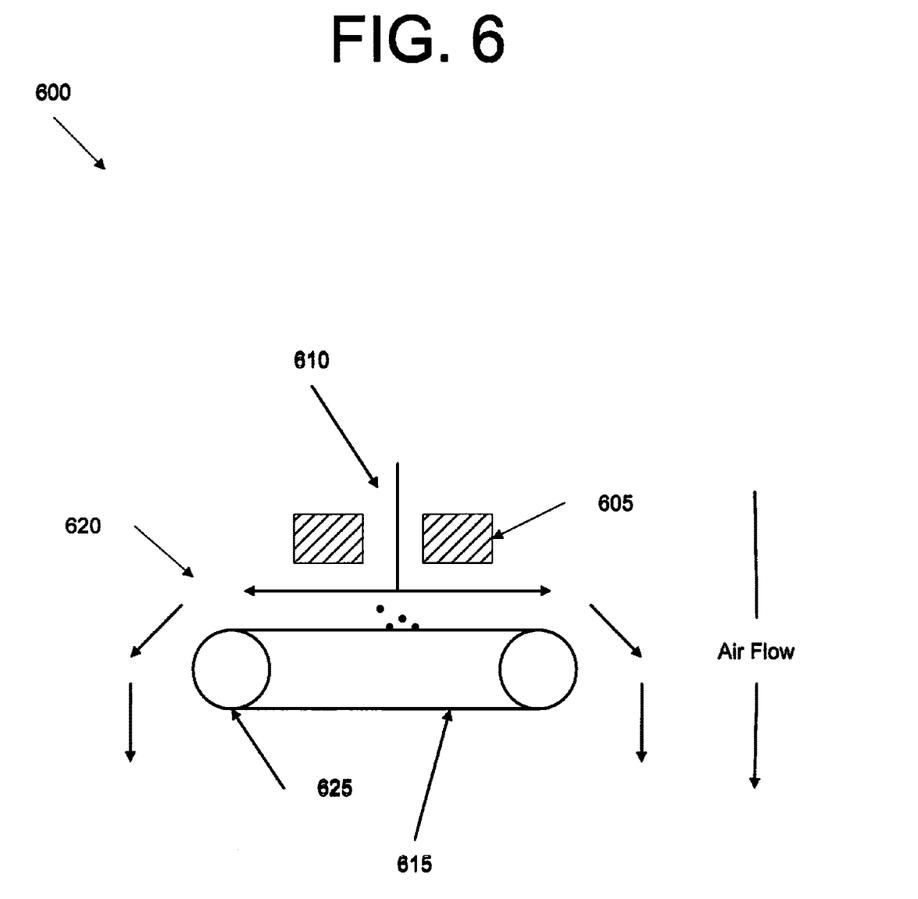
FIG. 6 illustrates a side view of a cross-section of the impactor shown in FIG. 4, according to an embodiment of the present invention.

FIG. 6 illustrates a side view of a cross-section 600 of impactor 400 shown in FIG. 4, according to an embodiment of the present invention. Cross-section 600 shows particles in the air being captured by a collector belt 615 as the particles traverse through an orifice 610 of impactor plate 605. The air flows through gap 620 and down to the next filter. Cross-section 600 also depicts a roller (or servo) 625 that allows collector belt 615 to rotate and be cleaned by the scraper depicted in FIG. 4. As the particles are removed from collector belt 615, a collection mechanism (not shown) may be used to collect the particles from collector belt 615. This allows the scraped particles to be taken to a lab, for example, for analysis purposes.

FIG. 7 illustrates a scroll filter 700, according to an embodiment of the present invention. Scroll filter 700 may be modular, such that a plurality of scroll filters can be stacked, or can be placed after or before one or more impactors. For example, an impactor set at thirty percent efficiency may be in front of a first scroll filter set at ninety percent efficiency followed by a second scroll filter set at ninety percent efficiency.

In this embodiment, a supply spool 705 includes material (or particle collector) 720, and a take up (or receiving) spool 710 is configured to receive material 720 when particle buildup is detected. A plurality of rollers 715 are used in this embodiment to move material 720 from supply spool 705 to receiving spool 710. It should be appreciated that each roller 715 may be connected via belt and/or pulley (not shown) for positive drive of material 720.

While this embodiment shows material 720 zigzagging over plurality of rollers 715, plurality of rollers 715 may be placed in any manner appreciated by a person of ordinary skill in the art, such that material 720 may move towards receiving spool 710 when particle buildup occurs. For instance, plurality of rollers 715 may be adjusted by mounting each roller 715 on slots in a housing (not shown), thus enabling changes in performance of scroll filter 700. When appropriately configured, it may be possible to make such changes in situ, thereby providing a measure of control over the filter performance to meet actual filtration needs of a mission.

Depending on the space between each roller 715, particles of different sizes may be captured by material 720. Also, the number of rollers 715 that are used may vary based on the size of scroll filter 715 and the size of the particles to be captured. Furthermore, any suitable material, e.g., industrial, commercial, etc., may be used to capture particles. For example, a high efficiency or a low efficiency material may be used depending on the particles that are to be captured. In other words, filter performance can be adjusted by using different materials, as well as altering the geometry and/or spacing of each roller.

In some embodiments, material 720 may be driven by an external or internal servo (not shown). In one embodiment, the servo may rotate the receiving spool 710, such that supply spool 705 may unwind a fresh set of material 702 each time a buildup of particles occurs on material 720. In another embodiment, the servo may rotate each roller 715, or any combination of supply spool 705, receiving spool 710, and rollers 715, such that supply spool 705 may unwind a fresh set of material 720 each time a buildup of particles occurs on material 720. In certain embodiments, one or more servos may rotate supply spool 705, rollers 715, and receiving spool 710, or any combination thereof, each time particle buildup occurs. The buildup of particles may be detected by, for example, a sensor (not shown) that detects the buildup, or a certain amount of weight, mass, inertia, pressure, or other means, on material 720. Upon detection, material 720 may be indexed and a fresh roll of material 720 may be released from supply spool 705 while material 720 including the particle buildup is received at receiving spool 710. By receiving used material at receiving spool 710, a collection history can be realized, such that one may determine what type of particles are collected and the efficiency rate of collection of the particles, as well as peak particle loading events over the period of operation. This not only enables improvements on the scroll filter device based on the collection history, but the possibility of removing the collected particles for analysis purposes may offer the potential for investigating the history of the particles collected, and as a result, may be used to refine the design of filtration systems in space habitats, space crafts, or commercial applications.

It should be appreciated that once all of material 720 is at receiving spool 710, material 720 may be removed from scroll filter 700 and new material may be inserted at supply spool 705. The new material may be unwound from supply spool 705, such that new material may then begin capturing particles through the air. This configuration increases the longevity of scroll filter 700, as well as any subsequent filter attached behind scroll filter 700. Also, the cost to replace scroll filter 700 is reduced, since only material 720 is being replaced.

In an alternative embodiment, the used material may be cleaned, or otherwise treated, for reuse, thus reducing the payload for material 720 over long space flights. For example, as used material is received by receiving spool 710, a scraper may be configured to remove the particle buildup such that the material can be reused. Such a configuration may provide an endless stream of material for continual use.

Figure 8:
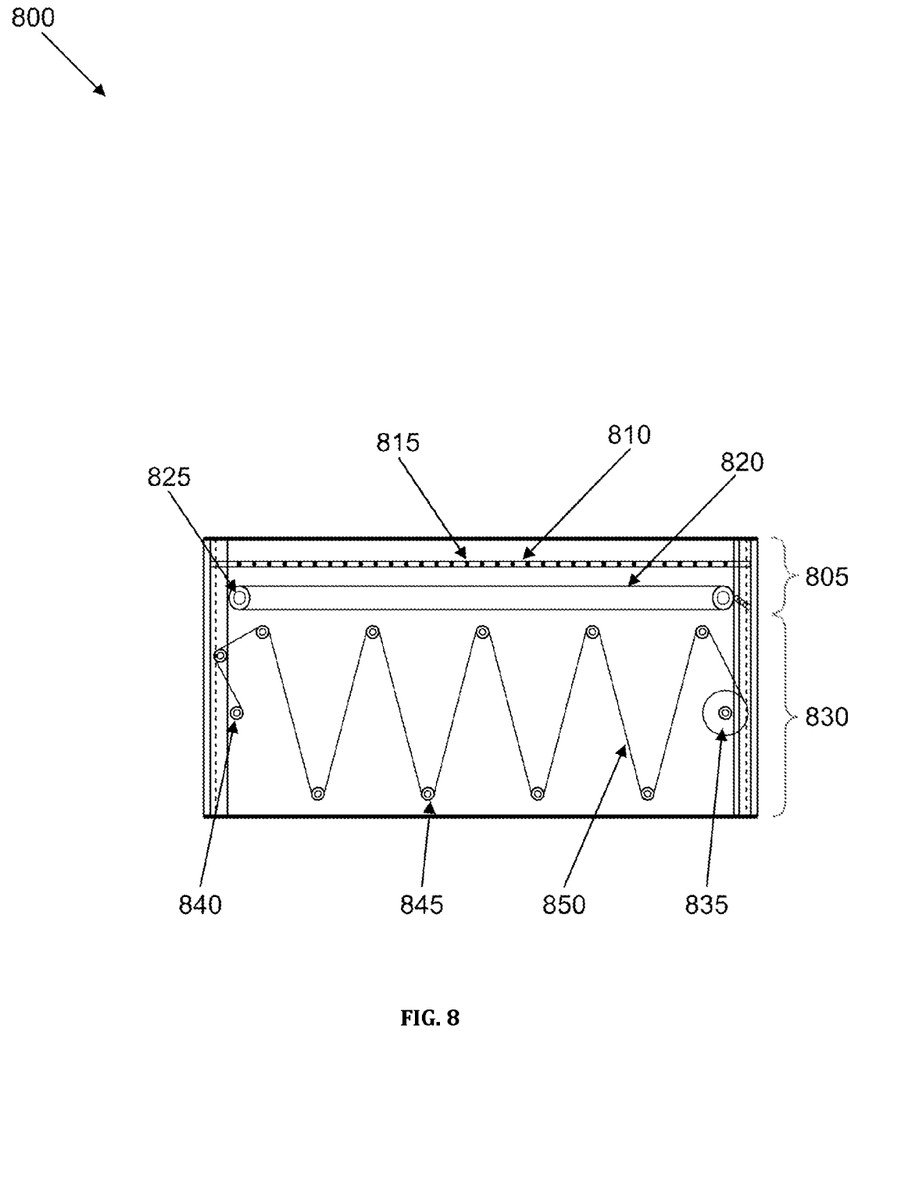
FIG. 8 illustrates a cross-section of a first stage impactor and a scroll filter, according to an embodiment of the present invention.

FIG. 8 illustrates a cross-section 800 of a first stage impactor 805 and a scroll filter 830, according to an embodiment of the present invention. In this embodiment, as air flows through a plurality of orifices 810 in an impactor plate 805, larger particles, for example, are collected by a plurality of collector belts 815. Rollers 820 can rotate collector belts 815 when particle buildup occurs.

Smaller particles that are not collected by, for example, collector belts 820 may be collected by material 850. As discussed in FIG. 7, material 850 may be oriented in a zigzag manner across a plurality of rollers 845. When particle buildup occurs, supply spool 835 can release unused material as the used material is wound up by receiving spool 840. This configuration allows for a pre-filtration device to be formed, collecting both larger particles and smaller particles prior to entering, for example, a HEPA filter or any subsequent filter. Such a configuration increases the longevity of the subsequent filter.

Figure 9:
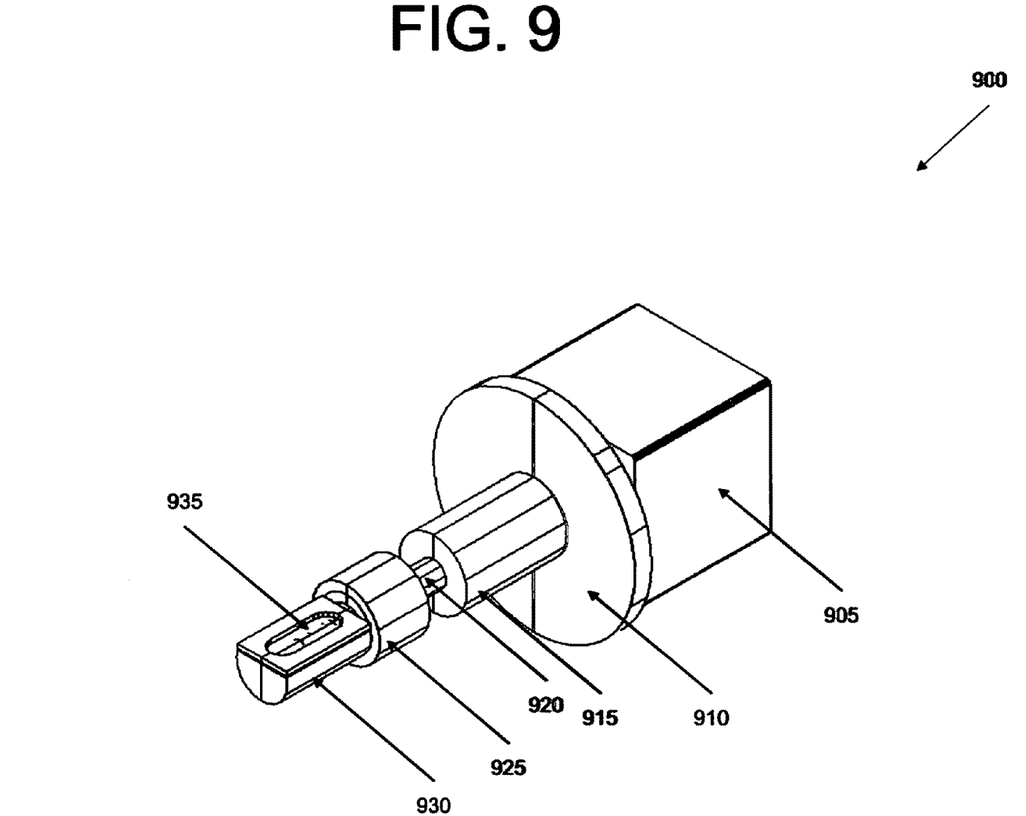
FIG. 9 illustrates a particle generator, according to an embodiment of the present invention.

In order to ensure that the above-described embodiments are fully functional, an in-situ particle generator may be used and operated in an air or gas closed system environment at non-standard or standard pressures. For example, FIG. 9 illustrates a particle generator 900, according to an embodiment of the present invention. Particle generator 900 includes a motor 905 that causes a drive shaft (not shown) to rotate a helical brush (also not shown) inside a particle sample cartridge 930. The rotation of the helical brush will be described in more detail below. It should be appreciated that while a helical brush is utilized in this embodiment, in other embodiments, different types of brushes or technology, such as a wiper, may be utilized that would achieve the same or a similar result of pushing particles through the screen of particle generator 900.

Particle sample cartridge 930 may be detachable and modular to allow particle samples of different sizes to be swapped. In other words, particle sample cartridge 930 may be swapped with another particle sample cartridge 930 containing different types of particles. Particle sample cartridge 930 may include a single type of particle, or multiple particles, depending on design choice. In some embodiments, particle sample cartridge 930 may include solid particle samples of different size, thus allowing impactors and scroll filters for different particle sizes to be tested. In other embodiments, particle sample cartridge 930 may include liquid based particles or a combination of solid and liquid based particles.

Particle generator 900 includes a mounting flange 910 and/or any sealing method or apparatus, as would be appreciated by a person of ordinary skill in the art, to mount and seal the internal cavity volume from the external environment. A first coupler 915 is used to couple, or hold together, the drive shaft, tube conduit 920, and the brush shaft. A second coupler 925 is used to couple, or hold together, the brush shaft and particle sample cartridge 930. Tube conduit 920 is used to protect the brush shaft from denigrating. When first and/or second couplers 915, 925 are removed, particle sample cartridge 930 can be removed or replaced with another particle sample cartridge.

Figure 10:
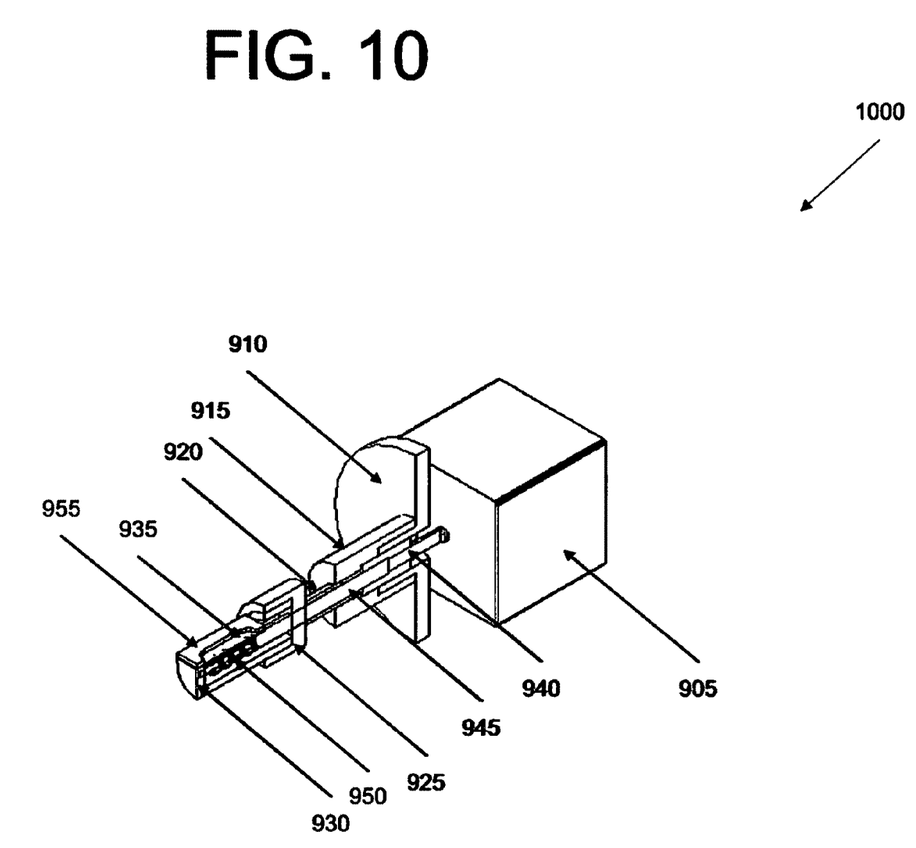
FIG. 10 illustrates a' cross-section of the particle generator shown in FIG. 9, according to an embodiment of the present invention.

FIG. 10 illustrates a cross-section 1000 of particle generator 900 shown in FIG. 9, according to an embodiment of the present invention. This embodiment shows a drive shaft 940 configured to drive brush shaft 945, thus causing a helical brush 950, for example, to rotate. For instance, motor 905 may cause helical brush 950 to rotate in alternating partial revolutions, such as a rocking motion, to drag particles back and forth across the length of screen 935. Based on the speed of rotation of helical brush 950, particles may be pushed through screen 935 at different rates. Screen 935 may be a mesh screen, or any type of screen that would be appreciated by a person of ordinary skill in the art. Also, the size of the mesh opening depends on the size of the particles that are being provided. The alternating motion prevents the particles from drifting towards a particular side of screen 935 or particle sample cartridge 930. This mode of operation can be sustained for a significant period of time for the duration of the test. To prevent screen 935 from moving, particle generator 900 also includes a flange 955 to hold screen 935 with particle sample cartridge 930.

Particles near screen 935 are continually pushed and ejected through screen 935 while the remainder of the particles move towards screen 935 due to settling and centrifugal effects from rotation. In certain embodiments, the face of screen 935 may be oriented or rotated relative to the flow direction to achieve optimal performance. For example, screen 935 can be rotated at different angles, such that screen 935 can be facing down, up, sideways, or a combination thereof.

When particles start to deplete from particle sample cartridge 930, motor 905 may increase the rotational speed, or create a larger arc revolution, of helical brush 950 to push particles through screen 935. As particles are pushed through screen 935, the particles may enter a flow duct or facility for testing of a multi-stage filtration device. The particles in particle sample cartridge 930 may be dragged across the length of the internal cavity and on screen 935, thus pushing the particles through screen 935, allowing the particles to enter, for example, the flow duct described above.

In one embodiment, an apparatus for generating particles is provided. The apparatus includes a particle cartridge containing particles of different sizes. The apparatus also includes a drive shaft configured to drive a brush, such that the particles of different sizes are pushed through a screen and into a filtration device or pre-filtration device.

In another embodiment, the particle cartridge can be replaced with another particle cartridge. The particle cartridge may include particles of same size.

In yet another embodiment, the motor may cause the drive shaft to drive the brush in an alternating motion, such that the particles of different sizes are moved back and forth across a length of the screen and pushed through the screen.

In a further embodiment, the motor may cause the drive shaft to increase a speed of rotation, or create a larger arc revolution, for the brush, such that the particles of different sizes are ejected at the same or different rates through the screen when the particles of different size start to deplete in the particle cartridge.

In another embodiment, the motor may cause the drive shaft to increase or decrease the speed of rotation for the brush, such that the particles of different sizes are ejected through the screen at a faster or slower rate.

In some embodiments, the screen may include holes of different sizes depending on the size of particles contained within the particle cartridge.

In an alternative embodiment, the screen may be swapped with another screen based on the sizes of the particles contained within the particle cartridge.

In certain embodiments, a face of the screen may be oriented in different directions, to produce different flow and particle settling effects in order to tighten or spread the spatial distribution of particles in the flow and/or to achieve different particle generation rates.

In other embodiments, the apparatus for generating particles may include an aerodynamic element or turbulence generating element attached or designed into the outside body (on the upstream side of the body) of the particle cartridge, such that different particle spreading rates in the flow can be achieved. For example, the turbulence generator element may increase the turbulent mixing of the particles in the flow, and therefore, increase the spreading rate of the particles. The aerodynamic element, for example, may reduce or constraint the spreading of particles.

It will be readily understood that the components of the present invention, as generally described and illustrated in the figures herein, may be arranged and designed in a wide variety of different configurations. Thus, the detailed description of the embodiments of an apparatus and a system, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of “certain embodiments,” “some embodiments,” or other similar language, throughout this specification refers to the fact that a particular feature, structure, or characteristic described in connection with the embodiment may be included in at least one embodiment of the present invention. Thus, appearances of the phrases “in certain embodiments,” “in some embodiments,” “in other embodiments,” or other similar language, throughout this specification do not necessarily all refer to the same group of embodiments, and the described features, structures, or characteristics may be combined in any suitable manner in one or more embodiments.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

We claim:

1. An apparatus, comprising:
   an impactor plate comprising a plurality of orifices configured to allow air to traverse through the plurality of orifices;
   a plurality of endless collector belts located adjacent to the impactor plate, the plurality of endless collector belts configured to collect particles in the air; and
   a gap between the impactor plate and the plurality of endless collector belts, wherein the gap is configured to cause air to traverse around and through the plurality of endless collectors belts while the particles are collected by the plurality of endless collector belts.

2. The apparatus of claim 1, wherein the plurality of orifices comprises a plurality of holes or rectangular slots.

3. The apparatus of claim 1, wherein, depending on a size of the gap, air traversing around and through the plurality of endless collector belts causes particles of different sizes to be collected.

4. The apparatus of claim 1, further comprising:
   a servo configured to rotate the plurality of endless collector belts when particle buildup occurs.

5. The apparatus of claim 4, wherein the servo is further configured to control a first set of rollers to unwind unused material on each band when particle buildup occurs, and control a second set of rollers to wind used material on each band when particle buildup occurs.

6. The apparatus of claim 1, further comprising:
   a scraper configured to remove particle buildup from the plurality of endless collector belts.

7. The apparatus of claim 1, further comprising:
   a sensor configured to detect particle buildup, or pressure resultant from the particle buildup due to particle mass on the plurality of endless collector belts.

8. The apparatus of claim 1, wherein particles of different sizes are collected depending on a size of each orifice and a distance between the impactor plate and the plurality of endless collector belts.

9. The apparatus of claim 1, further comprising:
   an adjusting unit configured to adjust a size of each orifice in situ, such that particles of different shapes and sizes can be collected.

* * * * *